United States Patent [19]
Roberts, II et al.

[11] Patent Number: 5,773,453
[45] Date of Patent: Jun. 30, 1998

[54] METHODS FOR ADMINISTRATION OF ANTILIPEMIC DRUGS

[75] Inventors: L. Jackson Roberts, II; Jason D. Morrow, both of Nashville, Tenn.; Eric H. Kuhrts, Woodside, Calif.

[73] Assignees: Vanderbilt University, Nashville, Tenn.; Lipoprotein Technologies, Inc., Woodside, Calif.

[21] Appl. No.: 425,057

[22] Filed: Apr. 19, 1995

[51] Int. Cl.⁶ .......................... A61K 31/44; A61K 31/19; A61K 31/415
[52] U.S. Cl. .......................... 514/356; 514/823; 514/568; 514/570; 514/420; 514/404; 514/405; 514/569
[58] Field of Search ...................... 514/356, 823, 514/568, 570, 420, 404, 405, 569

[56] References Cited

U.S. PATENT DOCUMENTS

| | | | |
|---|---|---|---|
| 4,965,252 | 10/1990 | Kuhrts | 514/54 |
| 5,023,245 | 6/1991 | Kuhrts | 514/54 |

OTHER PUBLICATIONS

Andersson, Rolf G.G. et al., Acta pharmacol. et toxicol., 41:1–10 (1977).
Ding, Reinhard W. et al., Am. Coll. Clin. Pharm., Abstract.
Ding, Reinhard W. et al., 2nd Cardio. Pharm. Int'l. Symp., Abstract 6.
Ding, Reinhard W. et al., Abstract 7a.
Ding, Reinhard W. et al., Abstract 7 (pp. 09.31).
Ding, Reinhard W. et al., Clin. Pharmacol. Ther., 46(6):642–647 (1989).
Hamazaki, Tomohito et al., Elsevier Scientific Publishers Ireland, Ltd. (1985).
Helgason, C. M. et al., Stroke, 25:2331–2336 (1994).
Kaijser, L. et al., Medical Biology, 57:114–117 (1979).
King, James M. et al., Am. J. Med., 97:323–331 (1994).
Kreisberg, Robert A., Am. J. Med., 97:313–316 (1994).
Lasagna, Louis, JAMA, 271:709–710 (1994).
McKenney, James M. et al., JAMA 271:672–677 (1994).
Morrow, Jason D. et al., J. Invest. Dermatol., 98:812–815 (1992).
Morrow, Jason D. et al., Prostaglandins, 38:263–274 (1989).
Stern, Ralph H. et al., Clin. Pharmacol. Ther., 50(1):66–70 (1991).
Svedmyr, N. et al., Acta pharmacol. et toxicol., 41:397–400 (1977).
Whelan, Anne Marie et al., J. Fam. Prac., 34(2):165–168 (1992).
Wilkin, Jonathan K. et al., Clin. Pharmacol. Ther., 31(4):478–482 (1982).
Wilkin, Jonathan K. et al., Clin. Pharmacol. Ther., 38(3):273–277 (1985).

*Primary Examiner*—Keith MacMillan
*Attorney, Agent, or Firm*—William B. Waker

[57] ABSTRACT

The present invention concerns methods for reducing cutaneous flushing in a patient to whom niacin is administered. According to the present method, two or more doses of a nonsteroidal anti-inflammatory drug are administered to a patient prior to administering niacin. Alternatively, the nonsteroidal anti-inflammatory drug can be administered concurrently with niacin administration. The nonstcroidal anti-inflammatory drug can be aspirin, ibuprofen, indomethacin, phenylbutazone, or naproxen. The nonsteroidal anti-inflammatory drug is administered in an amount effective to reduce cutaneous flushing caused by the niacin, and is administered in an amount up to 160 mg for aspirin and ibuprofen, 10 mg for indomethacin, and 100 mg for phenylbutazone and naproxen.

6 Claims, 4 Drawing Sheets

METHODS FOR ADMINISTRATION OF ANTILIPEMIC DRUGS

I. FIELD OF THE INVENTION

The invention concerns methods and compositions for administration of antihyperlipidemic (ie., hypolipemic or antilipemic) drugs, particularly nicotinic acid and its derivatives, while producing decreased flushing reaction.

II. BACKGROUND

Abnormally high levels of circulating lipids (hyperlipidemias) are a major predisposing factor in development of atherosclerosis. Elevated levels of serum cholesterol and cholesteryl esters, which are carried by the beta-lipoprotein or low density lipoprotein (LDL) and lipoprotein (a) (Lp(a)) fractions of serum lipids, are known to be atherogenic. Also implicated in cardiovascular disease are elevated levels of triglycerides, carried mostly in the very low density lipoprotein (VLDL) fraction.

Drugs which lower serum lipids (i.e., hypolipemic drugs) frequently are prescribed to retard development of atherosclerotic lesions in individuals exhibiting hyperlipidemias. Many of these drugs are effective when taken regularly, but suffer from poor patient compliance due to unpleasant side effects. Examples of effective but underutilized hypolipemic drugs include the bile acid binding resins, such as cholestyramine.

The ability of large doses of nicotinic acid (i.e., niacin) to lower serum lipid levels has been recognized for many years. This drug is unusually effective because it lowers the levels of several classes of morbidity-associated serum lipids, including LDL cholesterol (LDL-C), Lp(a), and triglycerides (Tg). In addition to its antilipemic activity, niacin is also an essential water-soluble vitamin. Nicotinic acid exhibits relatively low toxicity on a molar basis. However, the doses required to lower atherogenic serum lipids are quite large, on the order of 1–8 grams per day. At these levels, adverse side effects are frequent, and may include gastrointestinal disturbances such as nausea, heartburn, and diarrhea. However, the most frequent and prominent side effect is intense flushing, often accompanied by cutaneous itching, tingling, or warmth, and occasionally by headache. Although the flushing side effect is in general harmless, it is sufficiently unpleasant that patient compliance is markedly reduced. Often, 30–40% of patients cease taking nicotinic acid within days after initiating therapy. Consequently, significant efforts have been exerted to develop niacin analogs, dosage forms, and treatment protocols which minimize the flush reaction.

Tolerance to the flush reaction develops after a few days or weeks of repeated administration of nicotinic acid. One strategy for administration is to begin with low doses, i.e., 125 mg twice daily, then to increase the daily dose by increments of 30–100% after 1–6 weeks at each dose level; see, e.g., McKenney et al., *J. Am. Med. Assn.* (Mar. 2, 1994) 271:672–710. This procedure reduces but does not eliminate the flush reaction. Ibid. A further difficulty with relying upon tolerance for suppression of the flush reaction is that tolerance is lost rapidly if the drug is discontinued for a day or two. Consequently the dose must be reduced again when administration is resumed.

Another method of reducing flush is to administer a sustained release (SR) form of nicotinic acid. Sustained release preparations reportedly have a lower incidence of flushing and gastrointestinal side effects, and concomitantly greater patient compliance and tolerance; see King et al., *Am. J. Med.* (1994) 97:323–331, 329; Knopp et al., *Metabolism* (1985) 34:642–650; Alderman et al., *Am. J. Cardiol.* (989) 64:725–729. However, even SR preparations are not tolerated by a significant fraction of the patient population; see Luria et al., *Arch. Int. Med.* (1988) 148:2493–2495. Moreover, SR dosage forms are prone to induce a much more severe side effect, hepatic toxicity; see, e.g., Rader et al., *Am. J. Med.* (1992) 92:77–81.

Recent studies have indicated that the flushing reaction is initiated by release of prostaglandin D2. Prostaglandins are known to cause vasodilation, as well as a subjective experience of discomfort. Evidence supporting the role of prostaglandin D2 in mediating the niacin-induced flush includes the observation that a dramatic rise in the concentration of prostaglandin F, a metabolite of D2, occurs in the blood coming from the skin following administration of niacin. Furthermore, the level of prostaglandin F2 decreases markedly after 6 days of continuous twice-daily administration of nicotinic acid. This decrease in nicotinic acid-induced prostaglandin F2 correlates with the development of tolerance to the flush reaction which usually develops upon prolonged administration. Therefore tolerance appears to reflect a decline in prostaglandin D2 release, rather than an increase in metabolic inactivation of nicotinic acid.

The putative role of prostaglandins in mediating the flush reaction suggests that inhibitors of prostaglandin synthesis might be useful in preventing the flush reaction. Several nonsteroidal antiinflammatory drugs (NSAIDs) have been shown to inhibit the synthesis of one or more prostaglandins (PGs) by blocking the enzyme prostaglandin synthetase, also referred to as cyclooxygenase. Among the NSAIDs in clinical use are aspirin, ibuprofen, naproxen, phenylbutazone, indomethacin, and flufenamic acid and its congeners. These NSAIDs inhibit the synthesis of PGs such as E2 and F2, but typically at high micromolar (uM) concentrations; see, e.g., Flower, *Pharmacol. Rev.* (1974) 26:33 (Table 1 therein).

The prostaglandin synthetase inhibitors aspirin and indomethacin have been shown to reduce the cutaneous flush induced by nicotinic acid. Anderson et al. (1977) *Acta Pharmacol. Toxicol.* 41:1–10, demonstrated that nicotinic acid-induced flush in guinea pigs, as measured by an increase in ear temperature, was inhibited by pretreatment at 4.5 and 0.5 hr with indomethacin (25 or 50 mg/kg) or aspirin (50, 100, or 200 mg/kg). An aspirin total dose of 975 mg, administered to human subjects in a divided dose of 650 mg at 1 hr and 325 mg at 0.5 hr prior to high dose nicotinic acid challenge, was shown to significantly reduce cutaneous flush; see Wilken et al. (1982) *Clin. Pharmacol. Ther.* 31:478–482.

A nicotinic acid ester derivative, methyl nicotinate, which causes local cutaneous erythema when administered topically, was used to study the flush-inhibiting effects of aspirin.

III. SUMMARY OF THE INVENTION

The present invention provides methods for administration of hypolipemic amounts of nicotinic acid or its congeners whereby the flush reaction is lessened or suppressed. The method involves pretreatment of a subject with a nonsteroidal antiinflammatory drug (NSAID) for a period of 1–6 days prior to beginning administration of nicotinic acid. Administration of the NSAID is continued during the period of administration of nicotinic acid.

NSAIDs of particular interest include salicylates such as aspirin and salicylate salts; propionic acids such as ibuprofen, fenoprofen, suprofen, benoxaprofen, flurbiprofen, ketoprofen, carprofen, naproxen, and sodium naproxen; indoleacetic acid derivatives such as indomethacin, sulindac, and etodolac; benzeneacetic acids such as aclofenac, diclofenac, and fenclofenac; pyrroleacetic acids such as tolmectin and zomepirac; anthranilic acids such as meclofenamate and mefenamic acid; pyrazoles such as oxyphenbutazone and phenylbutazone; and oxicams such as piroxicam. In certain preferred embodiments, the NSAID may be administered in dosages which are less than 25%, often less than 15%, frequently less than 10%, sometimes less than 5%, and even as little as 1–0.1%, of the usual antiinflammatory or analgesic dosage. For example, with respect to aspirin, the total daily dosage optionally may be as low as 10–160 mg, and commonly may be 20–100 mg, often 40–80 mg. Administration of the daily total dosage in multiple doses of an immediate release (IR) formulation or in sustained release (SR) formulations is preferred.

IV. BRIEF DESCRIPTION OF THE DRAWINGS

FIG. 1 is a graph showing the increase in excretion of PGD-M, the major urinary metabolite of PDG2, in human subjects over 7 hr following ingestion of 500 mg nicotinic acid; triangles indicate subject 1, circles indicate subject 2, and squares indicate subject 3.

V. DETAILED DESCRIPTION OF THE INVENTION

Figure 1:
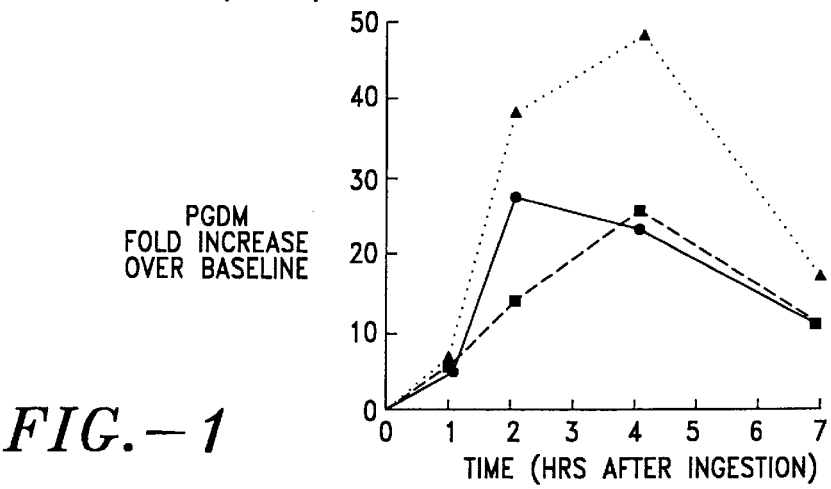

The present invention provides methods for administration of antihyperlipidemic amounts of nicotinic acid and its antihyperlipidemic congeners (herein collectively referred to as nicotinates) so that the flush reaction is lessened or prevented. The methods involve pretreatment of a subject with a nonsteroidal antiinflammatory drug agent (NSAID) in an amount sufficient to inhibit synthesis of prostaglandin D2 (PGD2) by monocyte-derived skin cells, especially macrophage-like cells such as Langerhans cells. The pretreatment is continued for a period of 1–6 days prior to administration of the nicotinate, preferably for at least 2 days, more preferably at least 3 days, and typically within the range of 2–4 days. Pretreatment beyond 3–4 days generally does not provide additional enhancement of the protection against flushing, but does preserve the protective effect and may be practiced within the scope of the invention.

During pretreatment the NSAID is administered in at least one dose daily, preferably 2 or more doses daily. In most cases, 4 or fewer doses are preferred, for the convenience and concomitantly improved compliance of the patient or subject. The dosage form may provide immediate release (IR) or sustained release (SR) of the NSAID. An SR dosage form may be administered fewer times daily than a comparable IR form, while providing similar protective serum concentrations of the NSAID.

The methods further provide for continued administration of the NSAID while the nicotinate is being taken. The nicotinate may be taken initially at a dosage level which is sufficient to produce hypolipemic effects in the subject, or may be taken initially at a lower level and raised progressively to hypolipemic dosage levels. This latter procedure allows induction of nicotinate tolerance to occur simultaneously with inhibition of flush by a NSAID.

A preferred nicotinate is nicotinic acid itself, which optionally may be provided as a salt. Other hypolipemic nicotinates include esters of nicotinic acid, such as lower alcohol esters (e.g., methyl, ethyl, or propyl esters).

When the nicotinate is an IR form of nicotinic acid itself, a hypolipemic dose level typically is at least 500 mg per day, often at least 500–750 mg or 750 mg–1 g, 1–1.5 g, or even up to 1.5–2 g daily. SR forms of nicotinate may be administered in lower dosages, often one-half the IR dosage. The daily dosage of nicotinate frequently is divided into multiple doses taken, e.g., 2–4 times daily. For purposes of defining the invention, a "hypolipemic amount" of nicotinate includes an amount which initially may be less than the amount which produces clinically significant hypolipemia, e.g., less than 500 mg for an IR form, provided that the daily dose is increased over time to a clinically effective hypolipemic amount. This allows for development of tolerance in conjunction with use of NSAIDs to lessen flush. An initial dosage of a subtherapeutic but tolerance-inducing amount of nicotinate typically will be capable of provoking at least some flushing reaction, e.g., 50–200 mg. This dosage may be increased gradually until dosages of 500 mg or greater are achieved.

Particularly preferred NSAIDs include aspirin, phenylbutazone, ibuprofen, naproxen, and indomethacin. These may be administered in the usual dosage ranges for treatment of pain and inflammation. In preferred embodiments, the NSAID is administered in dosage ranges less than 25%, often less than 15%, 10%, 5%, 1% or even 0.1%, of the usual antiinflammatory or analgesic dosage.

An especially preferred NSAID is aspirin. Aspirin preferably may be administered in daily dosages of at least 10 mg, more preferably at least 20, 40, 60, or 80 mg, but alternatively may be administered at levels of 100, 120, 140, 160, or up to 325 or 650 mg daily. Even higher daily dosages of aspirin may be consumed and will tend to suppress flushing in accordance with the invention, but these dosages run some risk of provoking undesirable side effects such as gastrointestinal (GI) upset or even ulceration. Moreover, these higher dosages are not more effective than the preferred lower dosages; indeed, because they tend to interfere with the metabolism of niacin in the liver, higher doses of aspirin tend to increase the serum concentration of niacin and thereby exacerbate the flushing reaction. An especially preferred daily dose range of aspirin is 40–80 mg, which is sufficient for extensive inhibition of synthesis of PGD2 in Langerhans cells, but low enough to have little capacity to provoke untoward side effects. Dosages at the low end of the range, e.g., 10–80 or 10–40 mg daily, may be administered even to many patients who are sensitive to aspirin and who readily develop GI ulcers, etc. IR aspirin preferably is administered at least twice daily (i.e., bid), optionally three (tid) or four (qid) times daily. In particular preferred embodiments, an aspirin dose of 10–40 mg is administered twice a day.

Other preferred NSAIDs include ibuprofen, naproxen, phenylbutazone, and indomethacin. Dosages of these NSAIDs are sufficient to inhibit synthesis of PGD2 in skin macrophages (Langerhans cells), thereby decreasing the flush reaction. As with aspirin, these NSAIDs inhibit PGD2 synthesis in the skin at lower concentrations than are required for inhibition of synthesis of other PGs in nonskin tissue. For example, indomethacin is effective in reducing flush reaction at doses only 0.1%–10% as great as those used for general antiinflammatory effects.

Indomethacin is active in inhibiting flush in daily dosages as low as 2–25 mg, although up to 50, 100, 150, or even 200 mg daily may be taken. As with other NSAIDs, the daily dosage preferably is divided among 2, 3, 4, or more doses, or may be taken as one or more doses of an SR formulation. A preferred dosage range is 2–10 mg, including 2, 4, 5, 6, or 8 mg, preferably administered bid.

Ibuprofen is effective in inhibiting flush in a daily dosage range similar to that for aspirin, e.g., 5–160 mg, although higher doses are effective also. In certain embodiments, preferred daily dosages are 5–80 mg, often 10–50 mg, commonly 20–40 mg. The dosage usually is taken in a divided dose bid, tid, or qid.

Naproxen is active in suppressing flush at a daily dosage of as little as 5–100 mg, often within the range 10–80 mg, commonly 15–50 mg, typically 20–40 mg. As with other NSAIDs, multiple doses, e.g., bid, tid, or qid, are preferred. Alternatively, an SR dosage form may be administered. Higher dosages, e.g., within the usual antiinflammatory dosage range of 500–1500 mg, are also effective but not required.

Phenylbutazone is active in suppressing flush at a daily dosage of 1–100 mg, often 5–50 mg, commonly 10–25 mg. As with other NSAIDs, multiple doses, e.g., bid, tid, or qid, are preferred. Alternatively, an SR dosage form may be administered. Higher dosages, e.g., within the usual antiinflammatory dosage range of 300–600 mg, are also effective but not required. Dosages at the low end of the active range, e.g., 1–10 mg, are advantageous because of the incidence of side effects such as blood dyscrasias (e.g., granulocytosis, aplastic anemia).

SR dosage forms are commercially available for some NSAIDs. For example, a timed-release form of aspirin is available in tablet form from Glenbrook Laboratories; see, e.g., Physician's Desk Reference. The tablets contain aspirin in a microencapsulated formulation with guar gum, microcrystalline cellulose, and starch.

Other SR formulations may be prepared by conventional methods. Solid dosage forms such as tablets and capsules may be prepared by incorporating hydrophilic gums such as cellulose ethers, exemplified by methylcellulose, hydroxypropyl-methylcellulose, and sodium carboxymethylcellulose. These polymers control the release of a NSAID by diffusion out of and erosion of the gelatinous layer formed by hydration of the gum within the gut after oral administration. Sustained release tablets may be manufactured by direct compression of the mixture following blending or by conventional wet granulation methods. A blend comprising a polymeric gum, a diluent such as lactose, a NSAID, and a lubricant such as magnesium stearate may be mixed thoroughly (e.g., 30 min in a Hobart mixer) and compressed with a hydrulic press at pressures between 1,000–5,000 psi, resulting in a tablet having a hardness of 3–8 Kp. Capsules may be manufactured by filling shells with a similar blend. In general, the percentage of polymer may be varied between 20–80% (w/w).

VI. EXAMPLES

The following examples are illustrative of certain aspects of the invention; they are not to be construed as limiting the scope of the invention as a whole.

A. Example 1: Pretreatment with Single Dose Aspirin

Three subjects were administered 40 mg aspirin 1 hr prior to a single 500 mg dose of IR nicotinic acid (Squibb). All three experienced severe flushing with a sunburned appearance on the face and ears, and blotches on the palms. All reported a subjective sensation of cutaneous warmth. Urine samples obtained at intervals after niacin administration demonstrated excretion of significant amounts of PGD-M, the major urinary metabolite of PGD2, over the next 7 hr (FIG. 1), confirming the association between PGD2 release and flushing symptoms.

Figure 2:
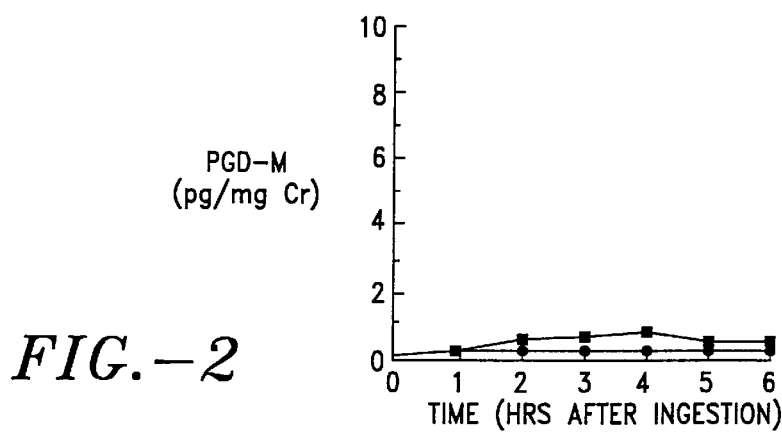
FIG. 2 is a graph showing the effect of 3 days of pretreatment with 40 mg aspirin on the excretion of PDG-M in human subjects following ingestion of 500 mg nicotinic acid.
Figure 3:
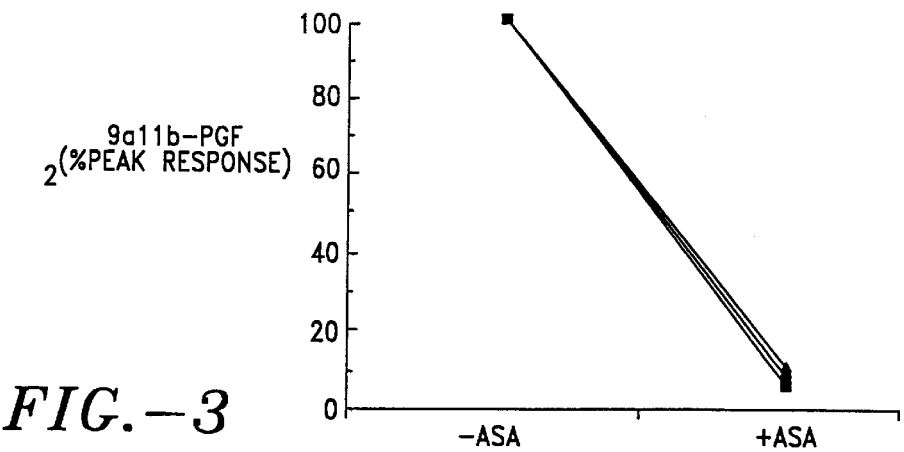
FIG. 3 is a graph showing the percent inhibition, with (B) or without (A) pretreatment with 40 mg aspirin, of PG release following topical application of nicotinic acid.

Two weeks later the same subjects were administered 40 mg aspirin for each of four days. On the fourth day, a single 500 mg dose of IR nicotinic acid (Squibb) was administered 1 hr after the aspirin. Two of the subjects experienced virtually no flushing. The third subject experienced some flushing, but less than that encountered previously without multiday aspirin pretreatment. Urinary excretion of PGD-M was much lower (FIG. 2), confirming the suppressive activity of aspirin on PGD2 release. Release of PGF2 after aspirin pretreatment (40 mg) was approximately 10% of baseline (FIG. 3).

B. Example 2: Pretreatment with bid Aspirin

Three subjects were administered 40 mg aspirin twice daily (i.e., bid) in the morning and evening for three days. On the fourth day, a 500 mg dose of IR nicotinic acid was taken with 40 mg aspirin. None of the subjects experienced any appreciable flushing.

Two weeks later the same subjects were administered a single dose of 500 mg nicotinic acid without aspirin. All three experienced severe flushing.

C. Example 3: Inhibition of PG Release in vitro

Figure 4:
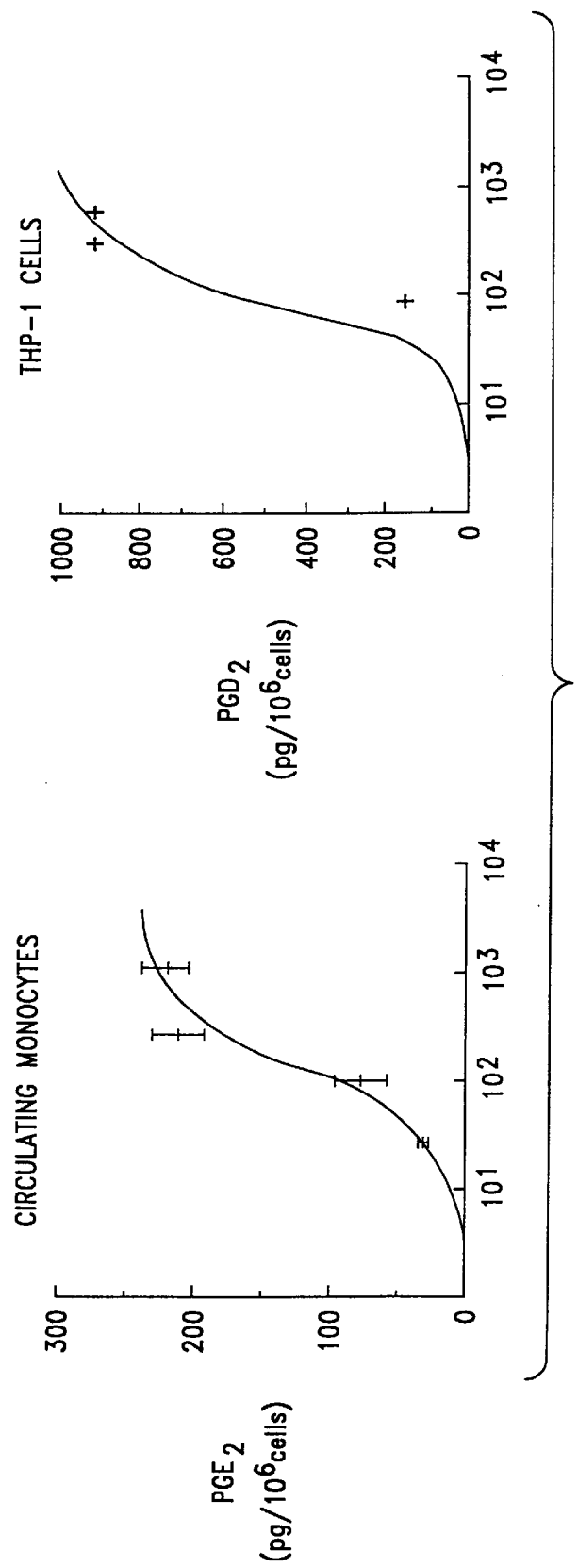
FIG. 4 is a graph showing the increase in release of PGE2 from circulating monocytes (panel A) and of PGD2 from cultured THP-1 cells (panel B) versus nicotinic acid concentration.
Figure 5:
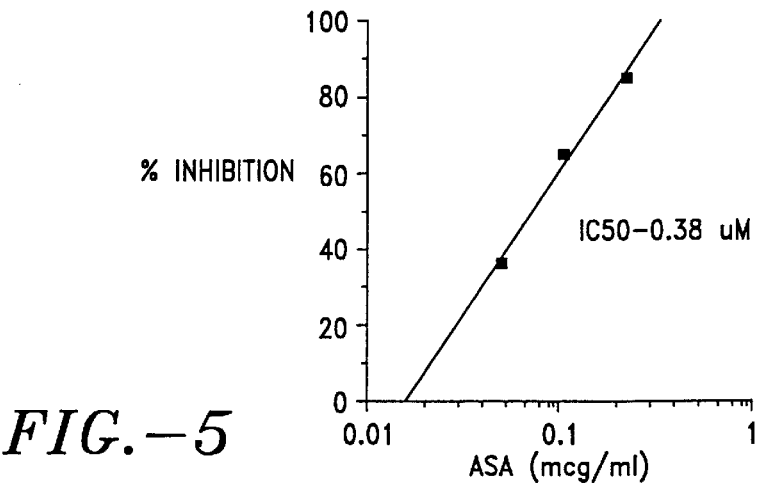
FIG. 5 is a graph showing a dose-response curve for inhibition of PG release from THP-1 cells by aspirin.

Niacin was shown to stimulate in vitro release of PGs from human circulating monocytes, which are precursors of macrophages, and from the human macrophage cell line THP-1 (FIG. 4). Aspirin in vitro inhibited niacin-stimulated release of PG from THP-1 cells with an IC50 of circa 0.38 micromolar (0.07 ug/ml) (FIG. 5). For comparison, a dose of 40 mg aspirin in an adult causes a peak plasma concentration of about 0.6 ug/ml. Thus the in vitro results are consistent with the clinical observation of inhibition of flushing with 40 mg aspirin.

D. Example 4: Inhibition of PG Release from Kupfer Cells in vitro

Figure 6:
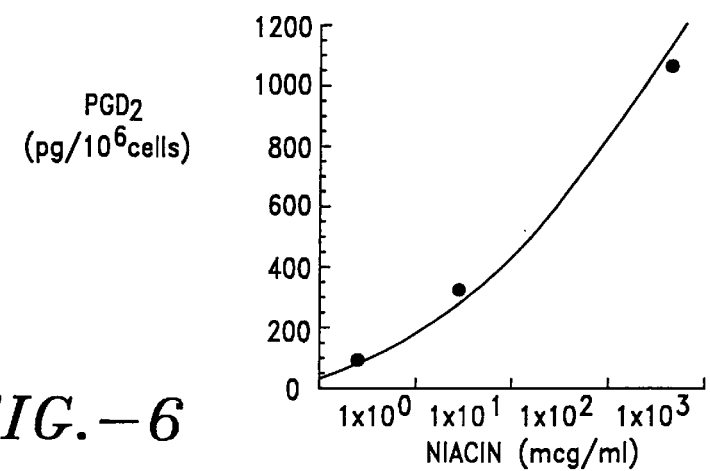
FIG. 6 is a graph showing release of PGD2 from Kupfer cells induced by various niacin concentrations.
Figure 9:
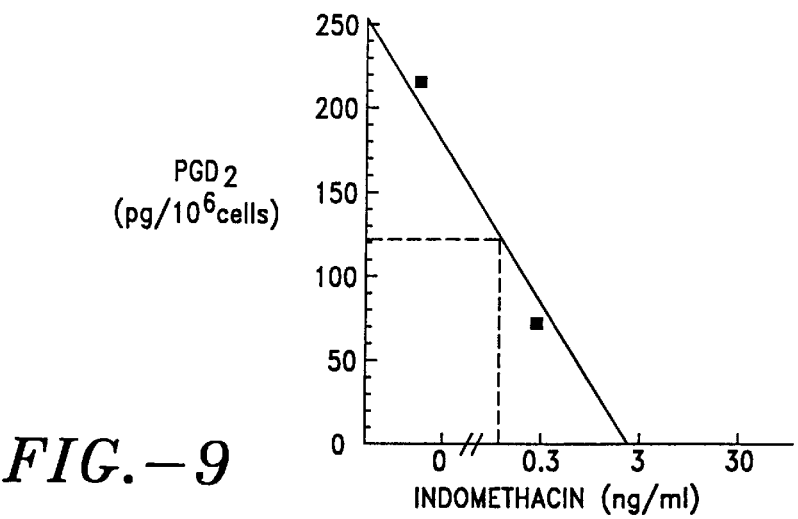
FIG. 9 is a graph showing inhibition of prostaglandin production in the human macrophage THP-1 cell line in vitro by indomethacin concentrations.

Kupfer cells, a type of macrophage found in the liver, were obtained from guinea pigs. Niacin stimulated release of PGD2 from Kupfer cells in vitro in a dose dependent manner (FIG. 6). This further supports the conclusion that macrophages are the source of PGs released by niacin administration in vivo.

E. Example 5: Niacin-stimulated Release of PG from Skin

Figure 7:
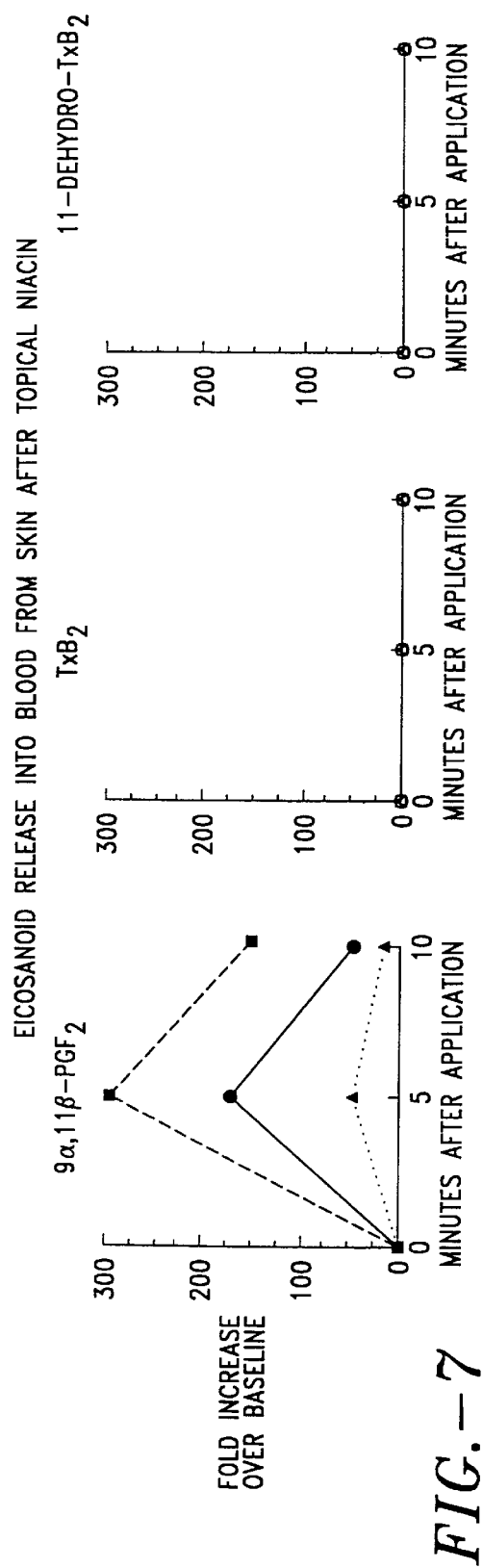
FIG. 7 is a graph showing release of eicosanoids into blood coming from the skin versus time after topical application of nicotinic acid; eicosanoids measured are 9α, 11β-PGF2 (panel A), TxB2 (panel B) and 11-dehydro-TxB2 (panel C).
Figure 8:
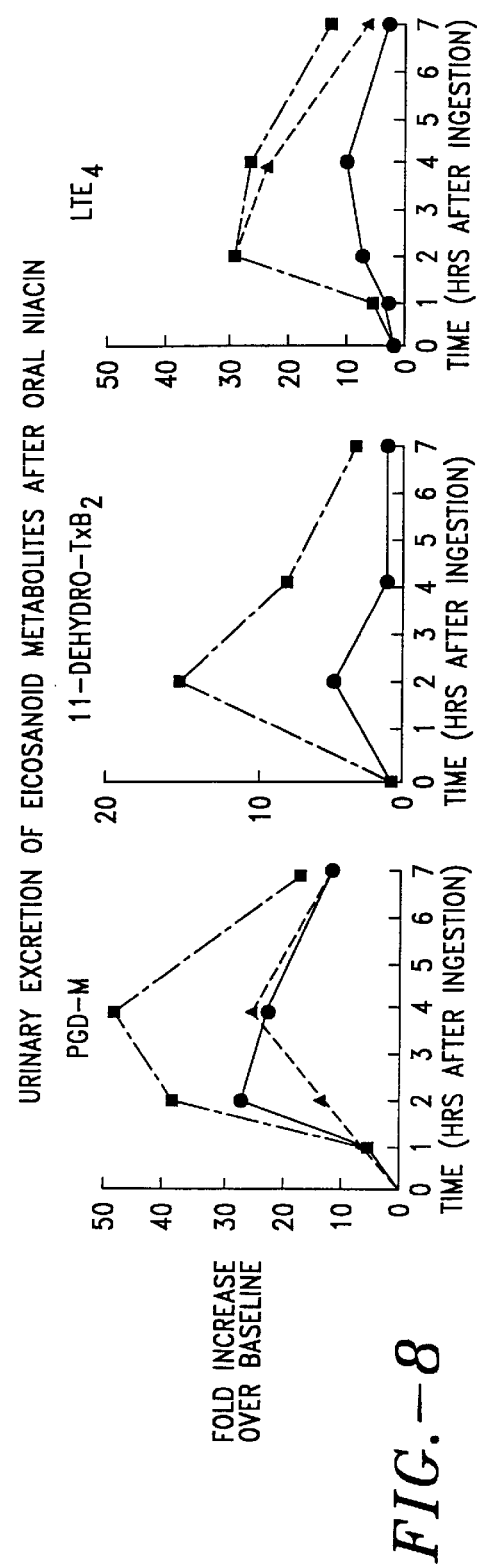
FIG. 8 is a graph showing urinary excretion of eicosanoid metabolites versus time after oral administration of nicotinic acid; eicosanoids measured are PGD-M (panel A), 11-dehydro-TxB2 (panel B), and LTE4 (panel C).

As further evidence that niacin -induced skin flushing is mediated by release of PGs, skin was treated with topical niacin, and release of eicosanoids into the efferent circulation was measured. Niacin increased the release of 9a, 11b-PGF2, a metabolite of PGD2, but did not release another eicosanoid, thromboxane (TxB2), which is also found in macrophages (FIG. 7). However, oral administration did result in increased amounts of metabolites of thromboxane and leukotriene as well as PGD2 in urine (FIG. 8). Langerhans cells, the macrophages of skin, may differ from other macrophages in releasing lesser amounts of eicosanoids other than PGD2.

F. Example 6: Pretreatment with Indomethacin in vitro

Indomethacin was used in place of aspirin to inhibit PG production in THP-1 cells in vitro as in Example 3. The IC50 was calculated to be approximately 1 nm. By contrast, inhibitory concentrations of indomethacin on PG production in other cell types are in the micromolar range. Thus THP-1 cells are approximately 1000 times more sensitive to indomethacin than are other cells. The dose of indomethacin required for in vivo inhibition of flushing is expected to be quite low as well. This confirms that low doses of NSAIDS other than aspirin are also effective in alleviating niacin-induced flushing.

VII. INCORPORATION BY REFERENCE

All publications and patent applications mentioned herein are explicitly incorporated by reference.

We claim:

1. A method of reducing cutaneous flushing in a patient to whom niacin is administered, comprising
administering to said patient two or more doses of an amount of a nonsteroidal anti-inflammatory drug effective to reduce cutaneous flushing caused by the niacin prior to administering the niacin,
wherein the nonsteroidal anti-inflammatory drug is a member selected from the group consisting of aspirin, ibuprofen, indomethacin, phenylbutazone, and naproxen, and
wherein the dose for each member is in the range shown below for that member:

| | |
|---|---|
| Aspirin | 10–160 mg |
| Ibuprofen | 5–160 mg |
| Indomethacin | 2–10 mg |
| Phenylbutazone | 1–100 mg |
| Naproxen | 5–100 mg. |

2. The method of claim 1, wherein the nonsteroidal anti-inflanmatory drug is administered for a period of 1–6 days prior to administering the niacin.

3. The method of claim 1, wherein the nonsteroidal anti-inflammatory drug is in immediate release dosage form.

4. The method of claim 1, wherein the nonsteroidal anti-inflammatory drug is in sustained release dosage form.

5. The method of claim 1, further comprising administering to said patient a dosage form consisting essentially of niacin and the nonsteroidal anti-inflammatory drug,
wherein the nonsteroidal anti-inflammatory drug is a member selected from the group consisting of aspirin, ibuprofen, indomethacin, phenylbutazone, and naproxen, and
wherein the nonsteroidal anti-inflammatory drug is present in an amount up to the amount shown below for that member:

| | |
|---|---|
| Aspirin | 160 mg |
| Ibuprofen | 160 mg |
| Indomethacin | 10 mg |
| Phenylbutazone | 100 mg |
| Naproxen | 100 mg. |

6. A method of reducing cutaneous flushing in a patient to whom niacin is administered, comprising concurrently administering to said patient a hypolipemic amount of niacin and a nonsteroidal anti-inflammatory drug,
wherein the nonsteroidal anti-inflammatory drug is a member selected from the group consisting of aspirin, ibuprofen, indomethacin, phenylbutazone, and naproxen, and
wherein the nonsteroidal anti-inflammatory drug is present in an amount effective to reduce cutaneous flushing caused by the niacin, and
wherein the nonsteroidal anti-inflammatory drug is present in an amount up to the amount shown below for that member

| | |
|---|---|
| Aspirin | 160 mg |
| Ibuprofen | 160 mg |
| Indomethacin | 10 mg |
| Phenylbutazone | 100 mg |
| Naproxen | 100 mg. |

* * * * *

UNITED STATES PATENT AND TRADEMARK OFFICE
CERTIFICATE OF CORRECTION

PATENT NO.   : 5,773,453                                              Page 1 of 1
DATED        : June 30, 1998
INVENTOR(S)  : Roberts, II et al.

It is certified that error appears in the above-identified patent and that said Letters Patent is hereby corrected as shown below:

Column 1,
Line 9, insert -- This invention was made with government support under grant number GM15431 awarded by the National Institute of Health. The government has certain rights in the invention. --

Signed and Sealed this

Eleventh Day of March, 2003

JAMES E. ROGAN
*Director of the United States Patent and Trademark Office*